US006245037B1

(12) United States Patent
Reum et al.

(10) Patent No.: US 6,245,037 B1
(45) Date of Patent: Jun. 12, 2001

(54) ROLLING SWAB APPLICATOR

(76) Inventors: Donald J. Reum, 1615 15th Ave., SE., St. Cloud, MN (US) 56304; Susan Reum Brundrett, 6281 Chalimar Rd., San Angelo, TX (US) 76904

( * ) Notice: Subject to any disclaimer, the term of this patent is extended or adjusted under 35 U.S.C. 154(b) by 0 days.

(21) Appl. No.: 09/156,524

(22) Filed: Sep. 17, 1998

(51) Int. Cl.[7] .......................... A61M 35/00; B05C 1/08; B05C 1/00

(52) U.S. Cl. .......................... 604/1; 15/230.11; 492/13; 492/19

(58) Field of Search .......................... 604/1–3; 15/230.11; 492/19, 13

(56) References Cited

U.S. PATENT DOCUMENTS

| | | | | |
|---|---|---|---|---|
| 5,419,003 | * | 5/1995 | Tollasepp | 15/230.11 |
| 6,012,196 | * | 1/2000 | Weiss | 15/230.11 |

* cited by examiner

*Primary Examiner*—Dennis Ruhl
(74) *Attorney, Agent, or Firm*—Albert W. Watkins

(57) ABSTRACT

A rolling swab applicator is disclosed which includes an elongated handle that can be grasped by a user. A rotatable applicator head is mounted to the handle member for rotation relative thereto. The applicator head includes a layer of absorbent material that may be pre-saturated with a disinfectant or irrigant to be applied to a wound or incision. Alternatively, a dry absorbent swab can be used for debris pickup and drying of a wound or application of ointments.

20 Claims, 2 Drawing Sheets

ROLLING SWAB APPLICATOR

BACKGROUND OF THE INVENTION

Summary of the Invention

The invention broadly relates to devices for applying disinfectants and similar pharmaceutical preparations to incisions, wounds and the like, and is specifically directed to a rolling swab applicator for the purpose of applying tinctures and ointments, or as a dry swab for use as a pickup, to aid healing and to treat infection.

Surgical incisions and other tissue wounds must be carefully treated to prevent infection. For example, after surgery surgical incisions must be dressed and redressed periodically to facilitate healing. An important part of wound dressing is applying a disinfectant such as iodine, hydrogen peroxide or sterile normal saline to prevent infection. This is typically accomplished with the use of a swab applicator which may either be dipped in the disinfectant before application, or which may be prepackaged with the solution saturating the swab.

Conventional swab applicators typically include a handle and an applicator portion connected to the handle that is absorbent and capable of holding a quantity of the disinfectant. The disinfectant is applied by direct engagement of the applicator with the incision or wound.

As prescribed, the applicator is wiped or dragged directly over the wound to apply the disinfectant. If the applicator head is circular, an alternative approach is to manually roll the applicator head over the wound. This avoids the transfer of the infection from one portion of the wound to the other. However, conventional swab heads are typically small in circumference, non-rotating and fixed to the handle of the device. A person can manually rotate the handle and cause the swab to rotate as well, but the dexterity required to match the surface speed of the head to that of the handle is difficult and cumbersome.

The invention is directed to a rolling swab applicator in which the applicator head is capable of being rotated relative to the handle. Three embodiments are disclosed. In each case, the simple controlled pressure of the swab on the wound allows the swab to travel with the length of the wound as the handle is moved laterally. Controlling the pressure on the swab head on the wound determines the amount of solution wetting the wound, from minimal to flooding the wound with solution as the swab rolls.

In the first embodiment, a handle includes an applicator support in the form of an axially projecting split hub. The applicator consists of a spool that can be inserted over the hub for rotation thereon. An absorbent material such as cotton or open cell urethane is wound around the outer periphery of the spool to receive the disinfectant.

The second embodiment includes an elongated handle that is formed with an elongated central bore. The applicator includes a small elongated rod that is inserted into the bore for rotation relative to the handle. The rod is preferably retained in the bore by one or more detents. One end of the rod projects beyond the handle and carries an applicator head that is circular in cross section and which has absorbent material placed thereon.

The third embodiment is similar to the second in that it includes an elongated hollow handle that receives a shaft with a plurality of axially spaced bearings enabling the shaft to rotate relative to the handle. The shaft is held in place within the handle by a plug member that is inserted into one end of the shaft and which bears against the handle end in a retaining fashion. The opposite end of the shaft projects beyond the handle and carries an applicator head. An absorbent material is wound around or otherwise affixed on the applicator head.

In all three of the preferred embodiments, the applicator head rotates relative to a stationary handle, enabling a user to grasp the handle and roll the applicator head over the incision or wound. The absorbent material may first be dipped into a disinfecting solution, or the disinfectant may be applied directly to the absorbent material. Alternatively, the absorbent material may be pre-saturated with disinfectant, sterile normal saline, or ointment.

The assembled rolling swab applicator may be provided in different sizes and individually packaged, enabling the user to choose the correct size of the applicator based on the size of the incision or wound. In either case, the absorbent material directly engages the wound in a pressing rather than a wiping manner, depositing or irrigating disinfectant or other solutions directly onto the wound.

Use of the inventive rolling swab applicator is simple, easy and fast, requiring only opening of the package of an applicator of the appropriate size and rolling the disinfectant onto the incision or wound. The applicator is then discarded.

The structure and features of the inventive rolling swab applicator will be more fully appreciated from the drawings and specification.

DETAILED DESCRIPTION OF THE PREFERRED EMBODIMENT

Figure 1:
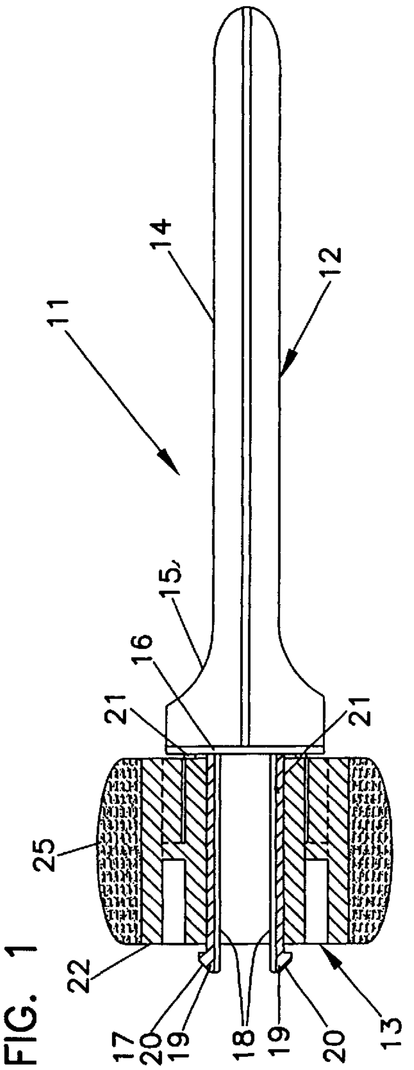
FIG. 1 is a view and side elevation of a first preferred embodiment of a rolling swab applicator.
Figure 2:
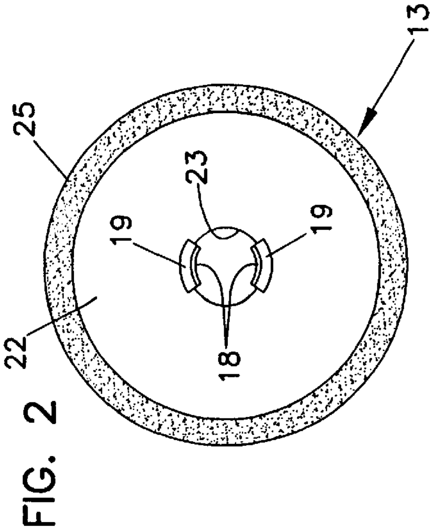
FIG. 2 is an end elevational view of the rolling swab applicator of FIG. 1.
Figure 3:
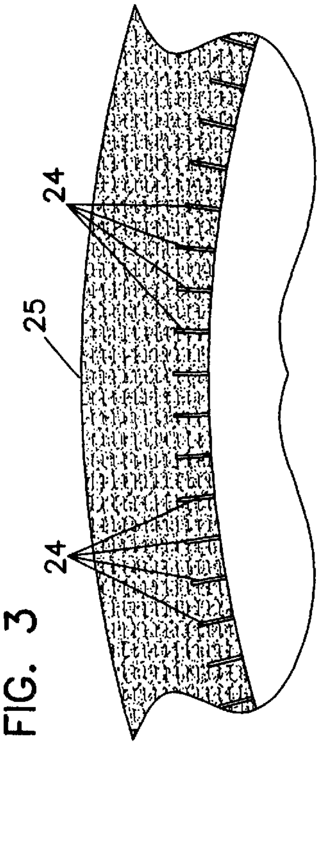
FIG. 3 is an enlarged fragmentary view of FIG. 2.

With initial reference to FIGS. 1–3, a first embodiment of the inventive rolling swab applicator is represented generally by the numeral 11. Applicator 11 includes a handle 12 and an applicator head 13, both of which are preferably formed by plastic injection molding.

Handle 12 is elongated and of sufficient length as to enable it to be grasped by a user. It includes a longer portion 14 of uniform cross section and an enlarged portion 15 that is flared from the portion 14 and terminates in a support disk 16.

Projecting axially forward from the support disk 16 is a split hub 17 consisting a pair of identical, axially projecting hub members 18. Each of the hub members 18 has an arcuate cross section to receive the circular applicator head 13 as discussed below. Hub members 18 are relatively stiff but nevertheless sufficiently resilient as to pinched together to permit the placement of applicator head 13 thereover. The extreme end of each of the hub members 18 is enlarged to define a retaining member 19 which is formed with a ramped or tapered surface 20 to facilitate placement of the applicator 13 as discussed in further detail below.

The front face of support disk 16 is formed with an annular boss or ring 21 that serves as a bearing surface for the applicator head 13.

Applicator head 13 takes the form of a solid spool 22 formed with an internal bore 23 the diameter of which is slightly greater than the external diameter of split hub 17. As best shown in FIG. 1, the width or axial depth of spool 22 is slightly less than the overall length of split hub 17; i.e., the axial dimensions between bearing ring 16 and the retaining members 19. As such, spool 22 may rotate on split hub 17 as well as relative to the bearing ring 21 on disk 16.

It will be appreciated that spool 22 may be placed on the split hub 17 by pressing the circumferential edge of bore 23 against the two ramp surfaces 20. This causes the split hub members 18 to be resiliently deflected inward to the point that spool 22 may slide over the retaining members 19 and onto the hub members 18. After spool 22 reaches the position shown in FIG. 1, hub members 18 resiliently return to the position shown, and spool 22 is retained by the backside of the retaining members 19.

With reference to FIG. 3, spool 22 has an outer circumferential surface 22 that is preferably circular but could be of other configuration provided it can be rolled over the incision or wound. The outer circumferential surface of spool 22 is preferably formed with a plurality of outwardly projecting small spikes 24 that are uniformly distributed thereover. A layer of absorbent material 25 is placed over the spikes 24 and retained thereby. Preferably, the absorbent material is a strip of cotton, a layer of open cell urethane or a suitable equivalent that is wound onto the outer circumferential surface of spool 22 with the spikes projecting into and retaining the cotton 25 as it wound. It is possible to secure the absorbent material 25 to spool 22 with the appropriate means, such as with an adhesive.

Materials other than cotton or open cell urethane may alternatively be used, provided they are capable of being sterile, relatively soft to avoid discomfort to the patient and sufficiently absorbent as to retain an appropriate disinfectant. As noted above, the disinfectant may be placed on the absorbent material at the time the rolling swab applicator is used, or the material may be pre-saturated with the disinfectant before packaging.

Figure 6:
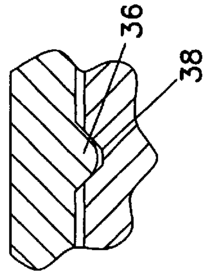
FIG. 6 is an enlarged fragmentary sectional view of the rolling swab applicator of FIG. 4 showing a detent arrangement.
Figure 5:
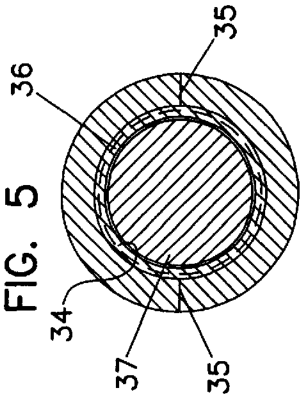
FIG. 5 is an enlarged transverse sectional view of the rolling swab applicator of FIG. 4.
Figure 4:
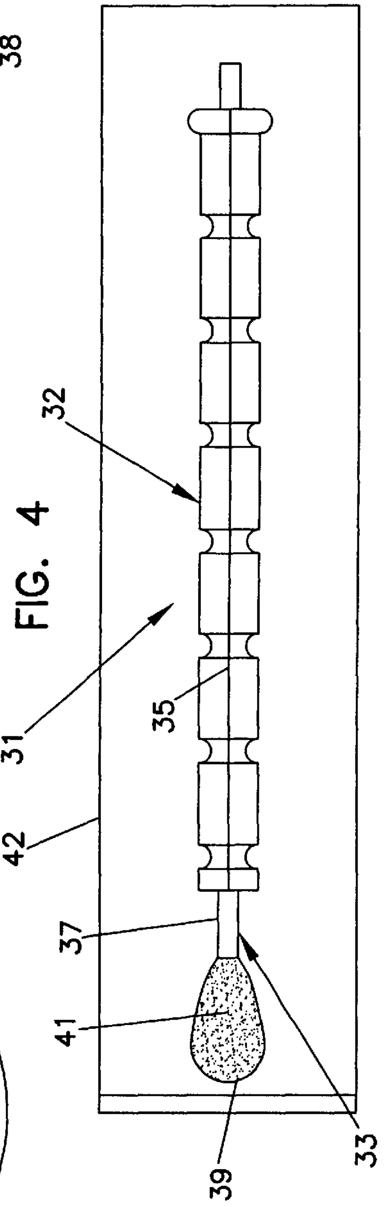
FIG. 4 is a side elevation of the second preferred embodiment of the rolling swab applicator.

The second preferred embodiment of the rolling swab applicator is shown in FIGS. 4–6 and bears reference numeral 31. Applicator 31 comprises an elongated handle 32 and an applicator head 33.

The handle 32 is generally cylindrical, having an irregular surface that facilitates its grasping. As shown in FIG. 5, it is formed with an elongated bore 34 that extends through the entirety of the handle 32. In the preferred embodiment, handle 32 is injected molded from plastic in identical halves, with the halves adhesively secured or bonded together along parting lines 35 (FIGS. 4 and 5). As shown in FIGS. 5 and 6, one or more annular circumferential beads 36 are formed on the inner circumferential surface of handle 32 for the purpose disclosed below.

The applicator 33 consists of an elongated thin rod 37 the length of which is greater than the axial length of handle 32. As shown on FIGS. 5 and 6, annular recesses 38 corresponding in number and size to the circumferential beads 36 are formed on the outer circumferential surface of rod 37 and axially spaced in the same manner as beads 36. This enables the rod 37 to be inserted into the bore 34 into the position shown in FIG. 4, with the annular beads 36 projecting into the annular recesses 38 in detent fashion. The relative sizing of the members 36, 38 is such that the rod 37 may rotate freely relative to the handle 32.

Applicator 33 further comprises an applicator head 39 that in the preferred embodiment is tear-shaped enabling it to access incisions and wounds in smaller areas. The applicator head 39 includes an outer absorbent material 41 of cotton, open cell urethane or the equivalent that can be wound onto the applicator 33 in the same manner as applicator 11, or slipped onto and adhesively secured to the end of rod 37.

Preferably, the absorbent material 41 of applicator head 39 is pre-saturated with a disinfectant, and the applicator 33 is encased in a sterile package 42. As an example, package 42 may be a bubble pack, a shrink wrap card or a clam shell package of injected molded plastic. It is essential that the applicator 31 be in a sterile condition at the time of packaging and that the package 42 maintain this sterility until the time it is opened and the applicator 33 used.

Figure 7:
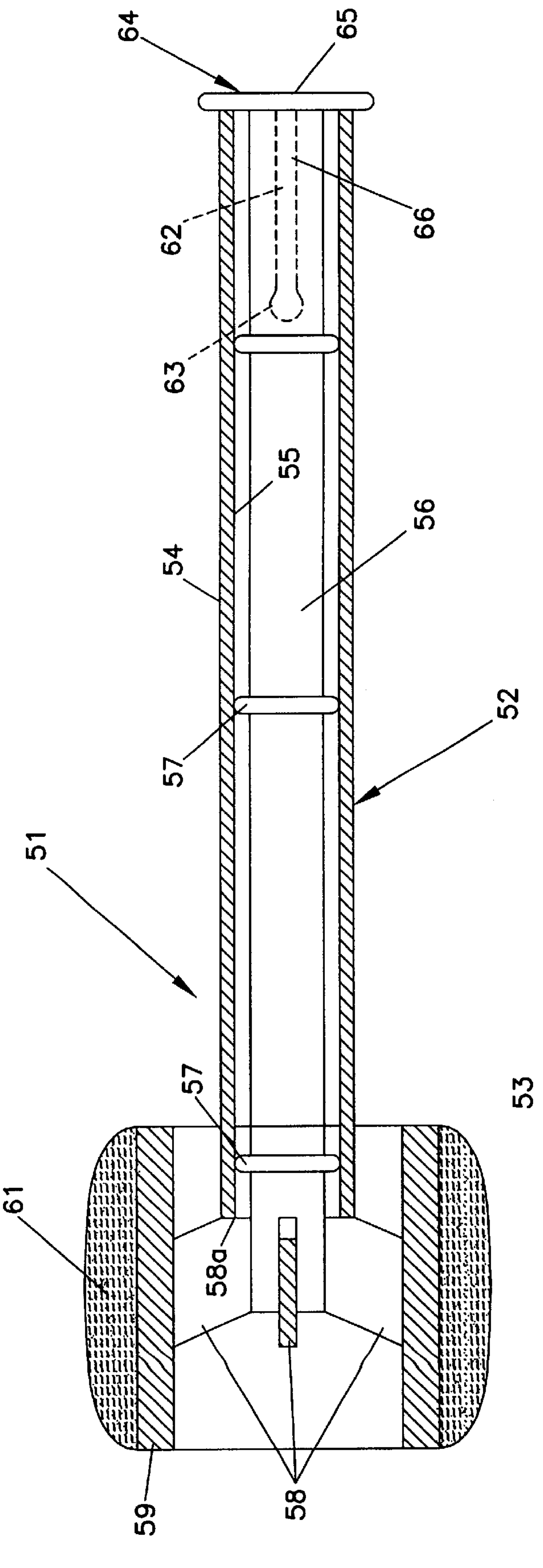
FIG. 7 is a side elevational view of the third embodiment of the rolling swab applicator.

The third preferred embodiment of the rolling swab applicator is shown in FIG. 7 and referred to generally by numeral 51. Applicator 51 includes a handle 52 and an applicator head 53.

Handle 52 comprises a cylindrical tube 54 having a relatively large internal bore 55 of uniform diameter. Tube 54 is preferably formed as a plastic extrusion.

Applicator head 53 includes an elongated shaft 56 of greater length than the tube 54 but having a diameter that is substantially less than the inside diameter of tube 54. Disposed at spaced axial intervals on shaft 56 are three annular bearings 57 that are sized and configured to permit the shaft 56 to rotate relative to the tubular handle 54.

As viewed in FIG. 7, the left end of shaft 56 projects beyond the handle 54 and supports three equiangularly spaced, radially projecting spokes 58. Each of the spokes 58 is formed with a short leg **58*a* that is perpendicular to shaft 56 and abuts the end of handle 54. The remaining portion of each of the spokes 58 then projects angularly outward to support a cylindrical spool 59. Spool 59 has a width or axial dimension such that it overlies a portion of the handle 54**.

Disposed on the outer circumferential surface of spool 59 is an absorbent material 61 which may be affixed with an adhesive, or through the use of small projecting spikes as in the embodiment of FIGS. 1–3.

The opposite end of shaft 56 terminates at the end of tubular handle 54 and is formed with a blind bore 62 extending axially inward from its right-hand end. The bore 62 is slightly enlarged at its inner most or blind end as shown at 63.

A retention plug 64 includes a circular head of disk-like configuration and an axially projecting pin 66 that has the same configuration as the bore 62 although slight smaller in dimension permitting it to be inserted into the bore 62. When the extreme enlarged end of the pin 66 reaches the enlargement 63 of bore 62 it is retained in detent fashion. This has the effect not only of retaining the end of shaft 56 in the position shown in FIG. 7, but also drawing the abutting edges 58a of spokes 58 against the left end of handle 54.

All three of the applicators 11, 31 and 51 are preferably pre-saturated with a suitable disinfectant and encased in a sterile package as described in connection with applicator 31. Further, the applicators 11, 31 and 51 are preferably manufactured in differing sizes, both with regard to the outer circumference of the applicator head as well as its width or axial length. In so doing, an applicator may be selected appropriate to the size of the incision or wound that is to be dressed, ensuring that the outer circumference of the applicator head is at least as large or greater than the length of the incision or wound to be dressed. This ensures the disinfectant or other solution will be placed over the entirety of the wound.

After selecting an applicator of appropriate size, the user simply opens the package, grasps the applicator handle, places the applicator head adjacent one end of the wound and rolls the applicator head over the entirety of the wound. The wound is thus covered with disinfectant or another appropriate solution that may work itself into all areas of the wound as the absorbent material of the applicator head is gently pressed into the wound. After application, the applicator is discarded.

It will be appreciated that the inventive rolling swab applicator can be quickly and easily used to place disinfectant or other solution over the wound.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A rolling swab applicator for placing a disinfectant on an incision or wound, comprising:

a handle member of sufficient size and appropriate configuration as to be grasped by a user;

a rotatable applicator head defining an outer applicator surface;

a layer of absorbent material secured to said applicator head and saturated with a disinfectant, said layer of absorbent material associated with said applicator surface for applying said disinfectant to said incision or wound; and rotatable mounting means for mounting the applicator head to the handle member for relative rotation thereto, the rotatable mounting means being constructed and arranged so that the applicator surface may engage the incision or wound and roll thereover.

2. The rolling swab applicator defined by claim 1, wherein the outer applicator surface is circular.

3. The rolling swab applicator defined by claim 2, wherein the outer applicator surface is continuous.

4. The rolling swab applicator defined by claim 3, wherein the layer of absorbent material comprises cotton.

5. The rolling swab applicator defined by claim 3, wherein the layer of absorbent material comprises open cell urethane.

6. The rolling swab applicator defined by claim 3, wherein said applicator head is formed with a plurality of small spikes projecting radially outward therefrom and distributed thereover, and the layer of absorbent material is wound over said spikes.

7. The rolling swab applicator defined by claim 1, wherein the handle member comprises an elongated handle having first and second ends, and the rotatable mounting means comprises a hub member disposed on the second end of the elongated handle, and the rotatable applicator head comprises a spool member rotatably carried on the hub member.

8. The rolling swab applicator defined by claim 7, wherein the handle member defines a predetermined axis of rotation and an enlarged bearing surface substantially perpendicular to the axis of rotation, and the hub member comprises first and second hub members projecting from the bearing surface parallel to said axis of rotation and defining a split hub, the first and second hub members being resiliently deflectable to receive said spool member.

9. The rolling swab applicator defined by claim 8, wherein an end of the first and second hub members distal to said bearing surface each comprises and enlarged retention member spaced from the bearing surface a predetermined distance, a length of the spool member parallel to said axis of rotation being less than said predetermined distance.

10. The rolling swab applicator defined by claim 9, wherein the enlarged retention members each comprise a ramp surface to facilitate mounting of the spool member on said split hub.

11. The rolling swab applicator defined by claim 1, wherein the handle member comprises an elongated handle with a circular bore therethrough, and the applicator head comprises a rod-like member insertable into said bore and rotatably carried thereby to define said rotatable mounting means.

12. The rolling swab applicator defined by claim 11, wherein one of said bore and rod-like member comprises a plurality of axially spaced annular beads, and the other of said bore and rod-like member comprises a like plurality of annual recesses sized and spaced to receive the annular beads in rotatable relation.

13. The rolling swab applicator defined by claim 12, wherein the rod-like member projects externally of the elongated handle defining a free end.

14. The rolling swab applicator defined by claim 1, wherein the handle member comprises an elongated handle with a circular bore therethrough, and the applicator head comprises a shaft insertable into said bore and rotatably carried thereby to define said rotatable mounting means.

15. The rolling swab applicator defined by claim 14, wherein the diameter of the shaft is less than the internal diameter of said bore, and the shaft comprises a plurality of annular bearing members having a diameter generally corresponding to the internal diameter of said bore to facilitate rotation of the shaft in said bore.

16. The rolling swab applicator defined by claim 15, wherein the shaft comprises first and second ends, the second end being formed with a blind bore having an enlarged portion, and the rolling swab applicator further comprises a retaining plug having a retaining head and retention pin, the pin configured to fit into said blind bore and to be retained therein, and said retaining head bearing against an end of the elongated handle with the pin inserted.

17. The rolling swab applicator defined by claim 15, wherein the shaft comprises first and second ends, the first end projecting axially from the elongated handle, and the applicator head further comprises a spool member mounted on said first end and defining said outer applicator surface.

18. The rolling swab applicator defined by claim 17, wherein the spool member comprises a plurality of spokes projecting radially and a cylindrical member carried by said spokes.

19. A sterile applicator for applying a medically appropriate solution to a person in a non-wiping manner, comprising:

a handle of sufficient size and appropriate configuration as to be grasped by a user;

a rotatable applicator head having a spool member and an axis of rotation;

an outer applicator surface circumscribing said rotatable applicator head;

a layer of absorbent material secured to said applicator head and associated with said applicator surface for absorbing said medically appropriate solution and, responsive to compressive forces, transferring said medically appropriate solution to said outer applicator surface; and rotatable mounting means for mounting said rotatable applicator head to said handle for relative rotation therebetween about said axis of rotation, said rotatable mounting means having a first bearing surface limiting motion of said rotatable applicator head in a first direction parallel to said axis of rotation and further having a first hub member and a second hub member, each of said hub members forming one part of a second bearing surface upon which said applicator head spool member may rotate;

said first and second hub members being resiliently deflectable to receive said spool member and further comprising enlarged retention members distal to said first bearing surface a predetermined distance, a dimension of said spool member parallel to said axis of rotation and adjacent said second bearing surface being less than said predetermined distance;

wherein said applicator surface engages said person and rolls thereover responsive to a physical contact between said applicator and said person and subsequent relative motion between said person and said applicator surface in a direction tangential to said applicator surface, whereby said medically appropriate solution may be dispensed in an amount dependent upon a magnitude of force of said physical contact in a non-wiping manner.

20. The sterile applicator of claim 19, wherein said enlarged retention members each comprise a ramp surface to facilitate mounting said spool member on first and second hub members.

* * * * *